United States Patent
Grand et al.

[11] Patent Number: 6,143,572
[45] Date of Patent: Nov. 7, 2000

[54] METHOD FOR DETECTING IMITATION GOLD, USING A PEN-LIKE DEVICE

[76] Inventors: Rami Grand; Ella Grand, both of 1669 E. 12th St., Brooklyn, N.Y. 11229

[21] Appl. No.: 09/151,242

[22] Filed: Sep. 14, 1998

[51] Int. Cl.[7] .................................................. G01N 33/20
[52] U.S. Cl. .............................. 436/80; 356/30; 422/61; 422/100; 422/101
[58] Field of Search ................................ 422/58, 61, 100, 422/101; 356/30; 436/76, 80

[56] References Cited

U.S. PATENT DOCUMENTS

| | | |
|---|---|---|
| 2,637,244 | 5/1953 | McLeod . |
| 3,615,747 | 10/1971 | Frieman ................................. 106/19 |
| 3,704,179 | 11/1972 | Ty et al. . |
| 3,952,030 | 4/1976 | Chambers et al. .................. 260/397.4 |
| 4,388,409 | 6/1983 | Reiss ....................................... 436/80 |
| 4,460,408 | 7/1984 | Badesha et al. .................. 423/510 X |
| 5,888,362 | 3/1999 | Fegan, Jr. ............................. 204/400 |

FOREIGN PATENT DOCUMENTS

| | | |
|---|---|---|
| 2124367 | 2/1984 | United Kingdom . |
| 97/10500 | 3/1997 | WIPO . |

OTHER PUBLICATIONS

M. Janghorbani et al. Anal. Chem. 1982, 54, 1188–1190, Jun. 1982.
K. Bicovsky et al. Chem. Abstr. 1989, 111, 82326h, Sep. 1989.

*Primary Examiner*—Arlen Soderquist
*Attorney, Agent, or Firm*—Goodman & Teitelbaum, Esqs.

[57] ABSTRACT

A pen-like device having a scriber for scratching a deep groove in a yellow colored, metal article object, such as jewelry, being tested for the gold content thereof, and an applicator provided on an opposite end of the pen-like device for conveying an acid solution, which is housed within the pen-like device, onto, around and in the groove to observe whether there is a color change to the testing area, on which the acid solution was applied, making the the testing area darker or black, where such a color change would indicate that the metal article or object is imitation gold, or has a gold content which is less than minimum karat requirement of the test. The acid solution includes a specific percentage of nitric acid which changes the color of the testing area when in contact with most imitation gold materials, preferably a specific percentage of hydrochloric acid to coact with the nitric acid, and a specific percentage of selenious acid which changes the color of the testing area when contacting a bronze or brass material. The specific percentage of each acid can easily be determined, for testing gold having a specific karat value.

8 Claims, 1 Drawing Sheet

METHOD FOR DETECTING IMITATION GOLD, USING A PEN-LIKE DEVICE

BACKGROUND OF THE INVENTION

The invention relates to a method for detecting imitation gold, and more particularly, to a pen-like device which is capable of scratching a groove in a surface of the metal article being tested, and then applying a specific acid solution on the test area including the groove to observe whether there is any color change to the metal surface on which the liquid was applied, where such a color change indicates that either the metal article is not gold or the gold content thereof has a karat value which is less than the minimum karat value required for the test.

Unfortunately, counterfeiting has become a way of life, costing governments and persons untold amounts of money. With respect to counterfeit paper currency, U.S. Pat. Nos. 5,063,163, 5,261,954 and 5,393,556 disclose methods of detecting counterfeit paper currency. These tests include applying a test solution having an initial color to any selected area of the paper currency being tested. Accordingly, for genuine paper currency, there will be no change to the color of the test area. However, counterfeit paper currency due to the starch content thereof, and the iodine content in the test solution, will turn the test area to a black coloration to indicate the currency is a counterfeit.

Gold is the most popular metal used for jewelry today. Pure gold is very soft so it is usually mixed with other metals (copper, silver, nickel, zinc) to form an alloy to make it stronger and prevent the easy bending thereof. Actually, all jewelry is made from a gold alloy and not from pure gold. Pure gold is always yellow, where any alloy is less yellow than the pure gold.

In order to ascertain the percentage of gold in an article, each gold alloy is measured by karats. Thus, pure gold is assigned a value of 24K, and one karat in the gold alloy is equal to ¹/₂₄ part thereof. Accordingly, 14K has 14 parts of pure gold therein, where the remaining 10 parts thereof are another metal such as copper, silver, zinc, nickel. Depending upon which metals are use in the alloys, a variety of colors can be produced. The higher the karat number, the closer the color is to yellow. Another practice is to plate low karat gold jewelry with a higher karat hold to improve the look thereof.

Many countries have established minimum standards that must be met for articles to be legally called "gold". The laws governing the actual content of gold required in a piece of jewelry, however, vary from country to country. In U.S.A. a "gold" article must be at least 10K. In England and Canada, the "gold" article must be at least 9K. In Italy and France, the "gold" article must be at least 18K. Thus, underkarating is a serious problem around the world.

U.S. Pat. No. 5,218,303 discloses a method of determining the amount of gold or other precious metal in an alloy by driving electrical pulses through an electrolyte wet junction. Additionally, U.S. Pat. No. 4,388,409 discloses a cement test device for detecting imitation gold by using a cast cement carrier impregnated with a complex acid solution, so that an imitation gold material presents a darkened blue color when placed in contact with a surface of the carrier.

Imitation gold has traditionally been detected by its solubility in concentrated nitric acid. When the nitric acid is applied to an area of most imitation gold materials, there is a color change where the area will become dark or black. However, it is found that the nitric acid has no effect on bronze or brass. Accordingly, if a bronze or brass material is made to have a gold appearance, then the nitric acid would not detect the imitation gold article. Usually, hydrochloric acid is added to the nitric acid to form an acqua regia acid solution, well known in the art.

Accordingly, there is presently a need for a method of detecting all types of imitation gold, such as those articles made of bronze or brass, and even those imitation gold articles plated with gold, where the test should be accurate and simple to use, as well as being portable and inexpensive.

SUMMARY OF THE INVENTION

Accordingly, it is an object of the present invention to provide means for detecting imitation gold which avoids the problems of prior art methods.

A further object of the present invention is to provide means for detecting imitation gold, which uses a pen-like device for first scratching a groove in a surface of metal material being tested, and then secondly for applying a specific acid solution on and around the groove for observing same to see whether or not a color change occurs, where such a color change would indicate that the metal material is not gold or that the gold content thereof is less then the minimum karat requirement of the test.

Still another object of the present invention is to provide means for detecting imitation gold, which includes an acid solution having nitric acid therein, and also preferably, hydrochloric acid for an aqua regia acid solution.

Yet another object of the present invention is to provide means for detecting imitation gold, which includes an acid solution as mentioned above, wherein the acid solution also includes selenious acid which changes color when contacting a bronze or brass material.

A still further object of the present invention is to provide means for detecting imitation gold wherein the specific karat content of the gold can be determined, for example, such as indicating whether the gold is 14K gold or 18K gold.

Another object of the present invention is to provide means for detecting imitation gold, which is simple to use, as well as being portable and inexpensive.

Briefly, in accordance with the present invention, there is provided a pen-like device having a scriber fabricated from a hard metal material for scratching a deep groove in the metal material being tested, and an applicator such as a felt tip being provided on the opposite end of the pen-like device so that a specific acid solution housed within the pen-like device can be conveyed through the applicator and applied onto and around the groove to observe whether there is a color change to the testing area, making the area darker or black. Such a color change of the testing area would indicate that the metal material being tested is imitation gold, or the gold content thereof is less than the minimum karat requirement of the test. Therefore, if the minimum karat requirement, which is determined by the specific percentages of the different acids in the acid solution, is for 14K gold, then an article made from 10K gold would then change to a darker or black color in the area where the acid solution is applied. On the other hand, if the article being tested is 18K gold or higher, there would be no color change in the area of the applied acid solution.

Preferably, the acid solution includes (1) a specific percentage of nitric acid which would change the color of the testing area to be darker or black when the nitric acid comes in contact with most imitation gold materials or with a gold article having a gold content less than the minimum karat requirement of the test, (2) preferably, a specific percentage of hydrochloric acid to coact with the nitric acid to form an aqua regia acid solution for use in a portable device, such as the above mentioned pen-like device, and (3) a specific percentage of selenious acid which changes the color of bronze or brass in the testing area to be darker or black. Accordingly, the specific percentage of each acid is easily determined, such as by trial and error, for testing gold having a specific karat value. Thus, when testing for 18K gold, the specific percentage of each acid would be higher than when testing for 14K gold, where it is not thought necessary to provide the specific percentage of each of the acids.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

In the various figures of the drawings, like reference characters designate like parts.

DESCRIPTION OF THE PREFERRED EMBODIMENT

The present invention is directed to means for detecting imitation gold. Pure gold, which is yellow in color, is usually too soft to be used by itself in forming an article or object, such as jewelry or a work of art. Accordingly, the pure yellow gold is combined with other suitable metals, such as copper, silver, etc., to form an alloy. In order to ascertain the percentage of gold in an article or object, the gold alloy is measured by karats. Thus pure gold is assigned a value of 24K, and each karat in the gold alloy is equal to 1/24 part thereof. Accordingly, 14K gold has 14 parts of pure gold therein, where the remaining 10 parts thereof are another metal, such as copper, silver, etc. In the United states, the minimum standard gold alloy for jewelry is 10K gold, where the standard minimum gold alloy in Canada is 9K gold, so that the standard varies according to country.

Figure 1:
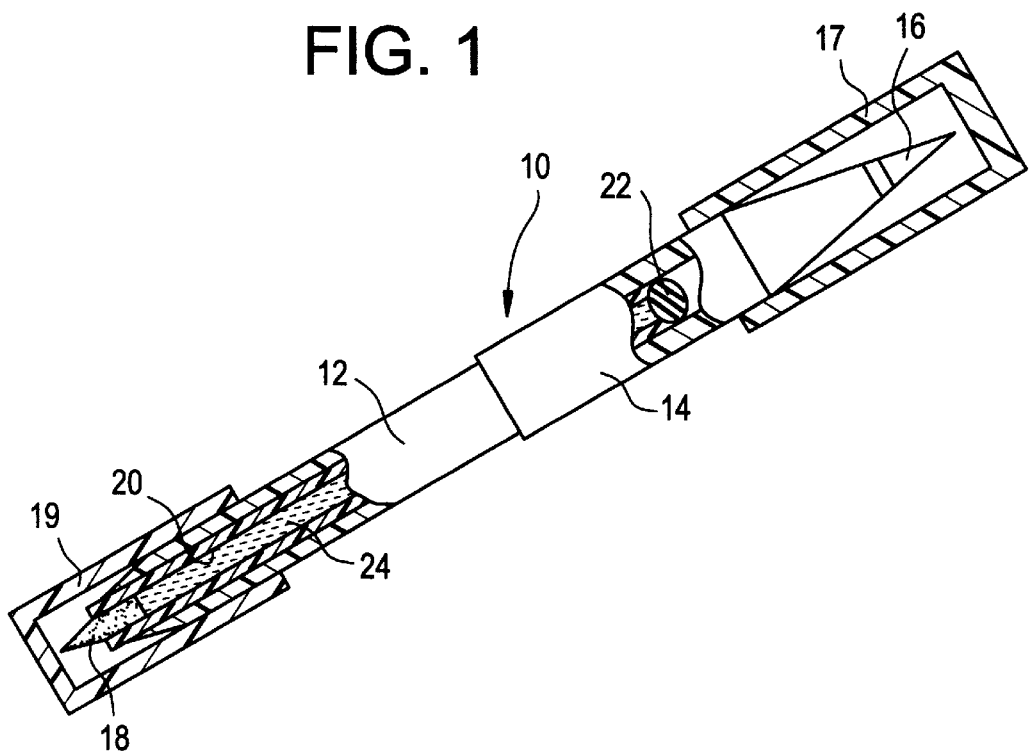
FIG. 1 is a perspective view, partly in cross section, of a pen-like device in accordance with the present invention.

Referring now to the drawings, FIG. 1 shows a pen-like device 10, in accordance with the present invention. The pen-like device 10 includes an elongated first part 12 which is removably secured by conventional means well known in the art, such as a snap-in connection, a threaded connection, etc., within a second part 14, in a similar manner as a conventional fountain pen. The second part 14 has a sharp pointed scriber 16, fabricated from a very hard metal material such as carbide, stainless steel, hardened tool steel, etc., on a free end thereof, for scratching a deep groove in the surface of the metal material of an article or object being tested, as set forth below. A conventional friction-fit removable cover 17 is provided on the free end of the part 14, to cover the scriber 16 when not in use so that the scriber 16 does not cause any harm or damage.

The first part 12 has an applicator 18 fabricated from a soft material, such as a felt tip, extending outwardly from the free end thereof. A conventional friction-fit removable cover 19 is provided on the part 12 to protect the applicator 18. The applicator 18 is secured in one end of a suitable, acid-resistant, cartridge or container 20. The opposite end of the cartridge or container 20 is provided with a removable, suitable acid-resistant, plastic or rubber-like stopper 22, well known in the art. The stopper 22 is secured in the opposite end of the cartridge or container 20, preferably in a friction fit, where obviously any other suitable securement means can be used in order to confine an acid solution 24 within the cartridge or container 20. The acid solution 24 is conveyed through the applicator 18 and applied onto, around and into the groove scratched made by the scriber 16 in the metal material of the article or object being tested in order to observe whether there is a color change, such as darker or black, to the testing area where the acid solution 24 is applied, as set forth below.

The acid solution 24 includes a predetermined percentage of nitric acid, which changes the color of the testing area to darker or black, when the nitric acid is applied to or in contact with most imitation gold materials. It is noted, that the percentage of nitric acid is changed according to the karat value of the gold which is sought during the test. Thus, if it is desired to test for 10K gold, a first selected percentage of the nitric acid would be used in the acid solution 24. Accordingly, if it is then desired to test for 14K gold, another acid solution 24 would be used having a higher percentage of nitric acid. As stated before, the percentages of nitric acid for a particular karat value of gold can be determined by trial and error, or from known percentages previously used for that particular karat value.

Additionally, a predetermined percentage of hydrochloric acid is preferably added to the acid solution 24 to coact with the nitric acid. It is well known that hydrochloric acid reduces the corrosiveness of the nitric acid. The hydrochloric acid and the nitric acid forms an aqua regia acid solution, well known in the art. Here again, the selected percentage of hydrochloric acid can be determined by trial and error, or by using the percentage thereof previously used in other similar acid solutions 24. Preferably, the aqua regia acid solution includes one part nitric acid and three parts hydrochloric acid.

A predetermined percentage of selenious acid is added to the acid solution 24 so that the acid solution 24 changes color of the testing area on the article or object, by turning darker or black, when applied to or when contacting an article made of bronze or brass material. As mentioned above, nitric acid does not change the color of the testing area when in contact with an article or object made of bronze or brass material so that the selenious acid is a necessary component of the acid solution 24. Here again, the specific percentage of the selenious acid can be determined by trial and error. Preferably, the selenious acid is 5 to 10 percent of the acid solution 24, depending upon the particular karat value of gold for which the test is being made. Thus, as indicated above, when testing for 18K gold, the specific percentage of both the nitric acid and the selenious acid would be higher than when testing for 14K gold. Preferably, the tester would have a different pen-like device 10 for each karat value of gold, such as having a first pen for 10K gold, a second pen for 14K gold, a third pen for 18K gold, and so on, until the tester has the desired number of pen-like devices 24.

Figure 2:
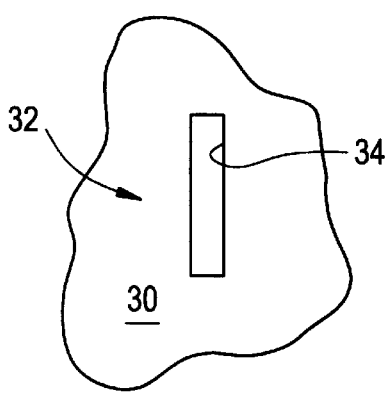
FIG. 2 is a fragmented top plan view of a surface of a metal article being tested for gold content in accordance with the present invention, having a deep groove scratched therein formed by a scriber of the pen-like device shown in FIG. 1.

FIG. 2 shows a surface 30 of a yellow colored, metal article or object 32, such as jewelry, which is being tested in accordance with the present invention. A deep groove 34 is scratched therein by the scriber 16 of the pen-like device 10 shown in FIG. 1, so that the groove 34 extends through any plating on the jewelry.

Figure 3:
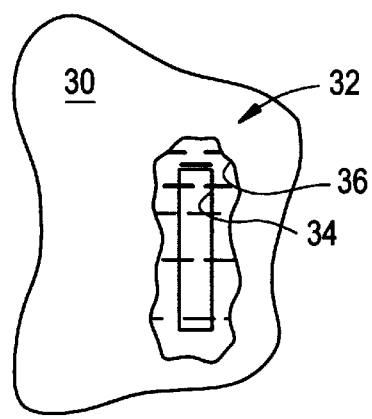
FIG. 3 is a fragmented top plan view similar to FIG. 2, where an acid solution has been applied over, around and into the scratched groove by an applicator of the pen-like device of FIG. 1.

FIG. 3 shows the same surface 30 of the yellow colored, metal article or object 32, where a portion 36 of the acid solution 24 has been applied over, around and in the groove 34 by the applicator 18 of the pen-like device 10 of FIG. 1 to cover the test area defined by the limits of the acid portion 36. In the test shown in FIG. 3, the test area, covered by the portion 36 of the acid solution 24, does not change color. Thus, if the tester was testing for 10K gold and used the appropriate pen-like device 10 for 10K gold, the test would indicate that the metal article or object 32 is solid gold of at least 10K gold, or gold of at least 10K gold plated with a higher karat gold such as 10K gold plated with 18K gold.

Figure 4:
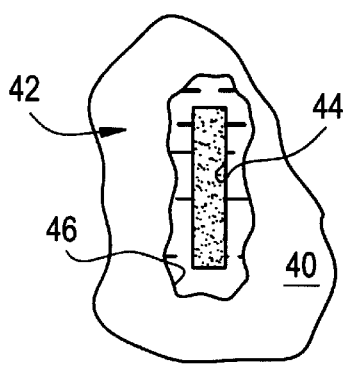
FIG. 4 is a fragmented top plan view similar to FIG. 3, where the acid solution has been applied over, around and into the scratched groove in a different metal article than the one shown in FIGS. 2 and 3.

FIG. 4 shows another test of a surface 40 of another yellow colored, metal article or object 42, such as jewelry, having a groove 44 scratched therein by the scriber 16, as mentioned above. The tester has used the applicator 18 to apply a portion 46 of the acid solution 24 on, around and in the groove 44. Accordingly, only that portion of the test area within the groove 44 has turned a darker color or black, where the remaining portion of the test area, on which the acid solution 24 was applied, has not changed color, as shown in FIG. 4. Here again, if the tester was testing for 10K gold, the test shown in FIG. 4 would indicate that the metal article or object 42 is gold plated with at least 10K gold, and that underneath part of the metal article or object 42, which was gold plated thereover, is imitation gold such as bronze brass, or gold which is less than 10K gold. Thus, for example, the article or object 42 could be 8K gold plated with 18K gold.

Figure 5:
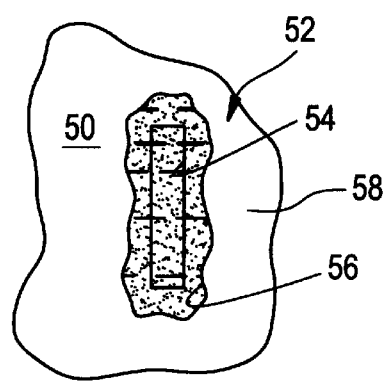
FIG. 5 is a fragmented top plan view similar to FIGS. 3 and 4, where the metal article being tested is different from each of the metal articles shown in FIGS. 3 and 4.

FIG. 5 shows yet another test of a surface 50 of still another yellow colored, metal article or object 52, such as jewelry, having a groove 54 scratched therein by the scriber 16, as mentioned above. The tester has again used the applicator 18 to apply a portion 56 of the acid solution 24 on, around and in the groove 54. Accordingly, the entire test area on the surface 50, covered by the acid portion 56, has turned a darker color or black, as compared to the remaining untested part 58 of the surface 50, as shown in FIG. 5.

Here again, if the tester was testing for 10K gold, the test shown in FIG. 5 would indicate that the metal article or object 52 is imitation gold, such as bronze or brass, or gold which is less than 10K. Furthermore, the entire metal article or object 52 could have been fabricated from an imitation gold, such as bronze or brass, or the metal article or object 52 could have been gold plated with less than 10K gold, or could even have been gold which is less than 10K gold. Therefore, if it is desired to know whether or not there is any gold in the metal article or object 52, the tester would have to use an acid solution 24 which tests for less than 10K gold.

Numerous alterations of the structures and method herein discussed will suggest themselves to those skilled in the art. However, it is to be understood that the present disclosure relates to preferred embodiment of the invention which is for the purpose of illustration only, and is not to be construed as a limitation of the invention.

What is claimed is:

1. A hand-held device for use in detecting imitation gold, comprising:

a hollow body including scriber means for scratching a groove in a test area surface of a metal article which is being tested for its gold content as compared to a minimum karat requirement;

said hollow body also including applicator means for applying a specific acid solution on the test area surface to observe any color change to the test area surface and to the groove therein;

said specific acid solution being housed within said hollow body in communication with said applicator means;

said specific acid solution including first acid means for changing color of bronze and brass when in contact therewith;

said first acid means being selenious acid; and said specific acid solution also including second acid means for changing color of imitation gold metal articles, other than bronze and brass, when in contact therewith;

said second acid means being a mixture of nitric acid and hydrochloric acid;

whereby a color change to any part of the test area surface, including the groove, making the part darker, indicates that the metal article being tested is imitation gold, or that its gold content is less than the minimum karat requirement of the test.

2. A hand-held device according to claim 1, wherein said scriber means is fabricated from a hard metal material, where said hard metal material is carbide, stainless steel or hardened tool steel.

3. A Hand-held device according to claim 1, wherein said applicator means is fabricated from a soft material, said soft material being a felt tip.

4. A hand-held device according to claim 1, wherein said second acid means includes one part of said nitric acid to three parts of said hydrochloric acid.

5. A hand-held device according to claim 1, wherein said selenious acid is 5 to 10 percent of said specific acid solution.

6. A method for detecting imitation gold, comprising:

scratching a groove with a pen scriber in a test area surface of a metal article being tested for its gold content as compared to a minimum karat requirement;

adding acid means, which changes color of bronze and brass, to a specific acid solution, the added acid means being selenious acid;

adding nitric acid to hydrochloric acid to form a mixture for changing color of imitation gold metal articles, other than bronze and brass, when in contact therewith;

adding said mixture to said specific acid solution;

applying said specific acid solution on the test area surface to observe any color change to the test area surface and to the groove therein;

whereby a color change to any part of the test area surface, including the groove, making the part darker, indicates that the metal article being tested is imitation gold, or that its gold content is less than the minimum karat requirement of the test.

7. A method according to claim 6, wherein three parts of said hydrochloric acid is added to one part of said nitric acid to form one of a series of mixtures used for detecting different gold karat grades.

8. A method according to claim 6, wherein said selenious acid is added to said mixture to form 5 to 10 percent of said specific acid solution.

* * * * *